United States Patent [19]

Gaüss et al.

[11] Patent Number: 4,644,000

[45] Date of Patent: Feb. 17, 1987

[54] MICROBICIDAL AGENTS CONTAINING 2-(1H-PYRAZOL-1-YL)-4-(3H)-QUINAZOLINONES

[75] Inventors: Walter Gaüss, Cologne; Hans-Joachim Kabbe, Leverkusen; Wilfried Paülüs, Krefeld; Hans-Jürgen Rosslenbroich, Monheim; Wilhelm Brandes, Leichlingen, all of Fed. Rep. of Germany

[73] Assignee: Bayer Aktiengesellschaft, Leverkusen, Fed. Rep. of Germany

[21] Appl. No.: 715,564

[22] Filed: Mar. 25, 1985

[30] Foreign Application Priority Data

Mar. 31, 1984 [DE] Fed. Rep. of Germany ....... 3412080

[51] Int. Cl.$^4$ ........................................... A61K 31/505
[52] U.S. Cl. ..................... 514/260; 544/284; 544/285; 544/287; 71/67; 71/92; 106/18.32
[58] Field of Search .......................... 514/260

[56] References Cited

U.S. PATENT DOCUMENTS 4,399,142   8/1983   Durant et al. ...................... 514/260

FOREIGN PATENT DOCUMENTS 2001534   3/1983   Fed. Rep. of Germany .

OTHER PUBLICATIONS

Shirakawa et al., "Chemical Abstracts", vol. 60, 1964, col. 12010h.
Kottke et al., "Chemical Abstracts", vol. 103, 1985, col. 103: 22541z.
Chemical Abstracts, Band 62, No. 9, Apr. 26, 1965, Spalte, 10451-c, Columbus, Ohio, US; & JP-A-64 23408 (Sankyo Co., Ltd.), 20-10-1964.

Primary Examiner—Glennon H. Hollrah
Assistant Examiner—James H. Turnipseed
Attorney, Agent, or Firm—Sprung, Horn, Kramer & Woods

[57] ABSTRACT

2-(1H-pyrazol-1-yl)-4-(3H)-quinazolinones of the formula

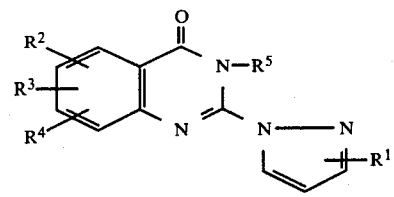

in which
$R^1$, $R^2$, $R^3$ and $R^4$ are identical or different and denote hydrogen, halogen, alkyl, alkoxy, hydroxyl or amino and
$R^5$ represents hydrogen or a cation,
are active compounds in microbicidal agents.

16 Claims, No Drawings

MICROBICIDAL AGENTS CONTAINING 2-(1H-PYRAZOL-1-YL)-4-(3H)-QUINAZOLINONES

The invention relates to microbicidal agents containing 2-(1H-pyrazol-1-yl)-4-(3H)-quinazolinones as active compounds.

It is known from Japanese Patent Specification No. 64/23,409 that 2-(1H-pyrazol-1-yl)-4-(3H)-quinazolinones have an action against tuberculosis.

East German Patent Specification 200,153/4 discloses that 2-(1H-pyrazol-1-yl)-4-(3H)-quinazolinones can be used as platelet aggregation inhibitors and as antihistamines.

Microbicidal agents have been found which contain, as the active compound, 2-(1H-pyrazol-1-yl)-4-(3H)-quinazolinones of the formula I

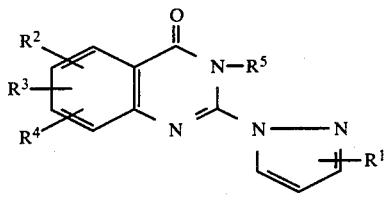
(I)

in which $R^1$, $R^2$, $R^3$ and $R^4$ are identical or different and denote hydrogen, halogen, alkyl, alkoxy, hydroxyl or amino and $R^5$ represents hydrogen or a cation.

Microbicidal agents in the context of the invention are employed not in the pharmaceutical field but for the protection of plants and preservation of industrial materials, preferably for the preservation of industrial materials.

In the context of the 2-(1H-pyrazol-1-yl)-4-(3H)-quinazolinones according to the invention, alkyl in general denotes a straight-chain or branched hydrocarbon radical with 1 to 12 carbon atoms. A lower alkyl radical with 1 to about 6 carbon atoms is preferred. The following alkyl radicals may be mentioned as examples: methyl, ethyl, propyl, isopropyl, butyl, isobutyl, pentyl, isopentyl, hexyl and isohexyl.

Alkoxy in general denotes a straight-chain or branched hydrocarbon radical which has 1 to 12 carbon atoms and is bonded via oxygen. A lower alkoxy radical with 1 to about 6 carbon atoms is preferred. The following alkoxy radicals may be mentioned as examples: methoxy, ethoxy, propoxy, isopropoxy, butoxy, isobutoxy, pentoxy, isopentoxy, hexoxy and isohexoxy.

Halogen in general denotes fluorine, chlorine, bromine or iodine, preferably fluorine, chlorine bromine and particularly preferably chlorine.

Cations in the context of the present invention include alkali metal and alkaline earth metal ions, preferably sodium, potassium, magnesium and caLcium, and ammonium.

Preferred microbicidal agents contain, as the active compound, 2-(1H-pyrazol-1-yl)-4-(3H)-quinazolinones of the formula II

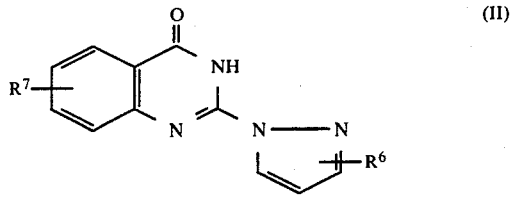
(II)

in which $R^6$ and $R^7$ are identical or different and denote hydrogen, fluorine, chlorine, bromine or lower alkyl.

Particularly preferred microbicidal agents contain, as the active compound, 2-(1H-pyrazol-1-yl)-4-(3H)-quinazolinones of the formula

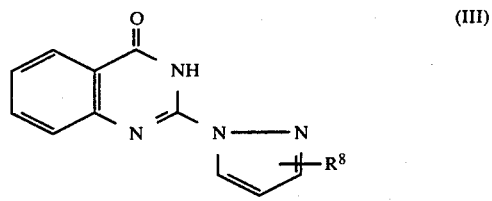
(III)

in which $R^8$ denotes hydrogen, or a methyl, ethyl or chlorine substituent in the 3- or 5-position.

It is furthermore preferable to use isomer mixtures of the 2-(1H-pyrazol-1-yl)-4-(3H)-quinazolinones in the microbicidal agents according to the invention. An isomer mixture of 2-(3-methylpyrazol-1-yl)-4-(3H)-quinazolinone and 2-(5-methylpyrazol-1-yl)-4-(3H)-quinazolinone is particularly preferred.

The preparation of the 2-(1H-pyrazol-1-yl)-4-(3H)-quinazolinones according to the invention can be illustrated, for example, by the following equation:

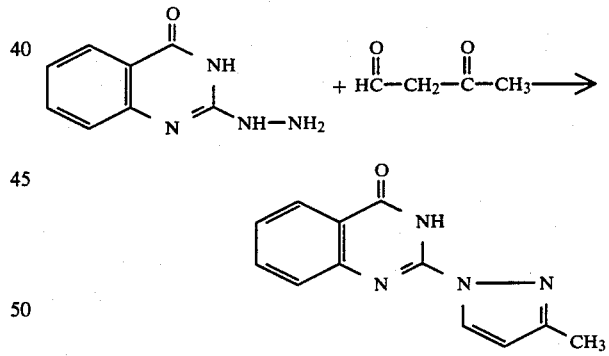

In this process, a 2-hydrazino-4(3H)-quinazolinone is reacted with a dicarbonyl compound or equivalents thereof: equivalents of the dicarbonyl compound which can be used are acetals, ketals, enolethers or enamines of the two carbonyl groups.

The method of pyrazole cyclization from hydrazine or its monosubstitution products with 1,3-dicarbonyl compounds or equivalents thereof is known in principle (Organic Syntheses 31, 43 (1951); Belgian Patent No. 656,016; H. Plümpe and E. Schegk, Archiv der Pharmazie 0, 704 to 708 (1967/8); German Offenlegungsschrift 2,158,490; and German Offenlegungsschrift 2,802,488). Another process for the preparation of the 2-(1H-pyrazol-1-yl)-4-(3H)-quinazolinones according to the invention can be illustrated by the following equation:

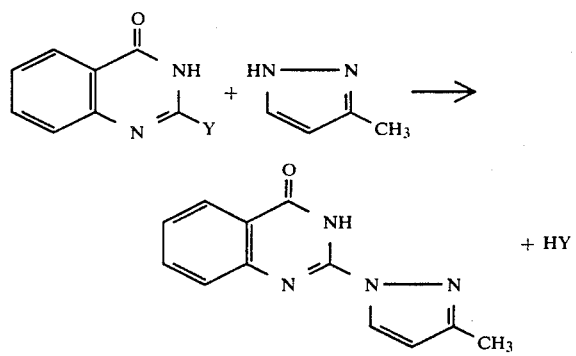

In this process, quinazolinones, in which Y represents a group which can undergo nucleophilic replacement, can be reacted with pyrazoles to give the end products according to the invention, HY being split off. The group Y which can undergo nucleophilic replacement represents, in particular, halogen, such as chlorine and bromine, an alkylmercapto group, an alkylsulphonyl group or the sulphonic acid radical ($SO_3H$).

The microbicidal agents according to the invention can essentially be used for the preservation of industrial materials and in plant protection.

According to the invention, industrial materials are materials which are not living and which have been formulated for use in industry. Industrial materials which are to be preserved by the active compound according to the invention from microbial change or destruction can be, for example, adhesives, sizes, paper and card, textiles, leather, wood, paints and articles made of plastic, lubricants and other materials which can be decomposed by microorganisms. In the context of the materials to be preserved, components of production plants, for example cooling water circulations, which can be impaired by microorganisms may also be mentioned. Industrial materials which may be mentioned as preferred in the context of the present invention are adhesives, sizes, paper and card, leather, wood, paints, cooling lubricants and cooling circulations. Examples which may be mentioned of microorganisms which can effect degradation of or a change to the industrial materials are bacteria, fungi, yeasts, algae and slime organisms. The active compounds according to the invention preferentially act against bacteria, moulds, in particular fungi which discolour and destroy wood (Basidiomycetes), slime organisms and algae.

Microorganisms of the following genera may be mentioned as examples: Alternaria, such as Alternaria tenuis, Aspergillus, such as Aspergillus niger, Chaetomium, such as Chaetomium globosum, Coniophora, such as Coniophora cerebella, Lentinus, such as Lentinus tigrinus, Penicillium, such as Penicillium glaucum, Polyporus, such as Polyporus versicolor, Aureobasidium, such as Aureobasidium pullulans, Sclerophoma, such as Sclerophoma pityophila and Staphylococcus, such as Staphylococcus aureus.

The active compound according to the invention can be converted into the customary formulations, such as solutions, emulsions, suspensions, powders, pastes and granules, depending on the field of application.

These can be prepared in a manner which is known per se, for example by mixing the active compounds with an extender consisting of a liquid solvent and/or solid excipients, if appropriate using surface-active agents, such as emulsifiers and/or dispersing agents, and, for example, if aqueous extenders are used, organic solvents, such as alcohols, can be used as auxiliaries, if appropriate.

Organic solvents for the active compounds can be, for example, alcohols, such as lower aliphatic alcohols, preferably ethanol or isopropanol, or benzyl alcohol, ketones, such as acetone or methyl ethyl ketone, liquid hydrocarbons, such as benzine fractions, and halogenated hydrocarbons, such as 1,2-dichloroethane. The microbicidal agents in general contain the active compounds in an amount of 1 to 95%, preferably 10 to 75%. The use concentration of the active compounds according to the invention depends on the nature and occurrence of the microorganisms to be combated, and on the composition of the material to be preserved. The optimum amount to be used can be determined by test series. In general, the use concentrations are in the range from 0.001 to 5% by weight, preferably 0.05 to 1.0% by weight, based on the material to be preserved.

The active compounds according to the invention can also be as a mixture with other known active compounds. The following active compounds may be mentioned as examples: benzyl alcohol mono(poly)hemiformal and other compounds which split off formaldehyde, benzimidazolyl methylcarbamates, tetramethylthiuram disulphide, zinc salts of dialkylthiocarbamates, 2,4,5,6-tetrachloroisophthalonitrile, thiazolylbenzimidazole, mercaptobenzothiazole, trialkyl-tin compounds, methylenebisthiocyanate and phenol derivatives, such as 2-phenylphenol, (2,2'-dihydroxy-5,5'-dichloro)-diphenylmethane and 3-methyl-4-chlorophenol.

The active compounds according to the invention are also suitable for use in plant protection agents.

Because of their fungicidal action, they can be used in plant protection for combating Plasmodiophoromycetes, Oomycetes, Chytridiomycetes, Zygomycetes, Ascomycetes, Basidiomycetes and Deuteromycetes.

Because of their bactericidal action, the active compounds according to the invention can be used in plant protection for combating Pseudomonadaceae, Rhizobiaceae, Enterobacteriaceae, Corynebacteriaceae and Streptomycetaceae.

The good plant tolerance of the active compounds in the concentrations necessary for combating plant diseases permits treatment of above-ground parts of plants, of vegetative propagation stock and seed, and of the soil.

EXAMPLES

Preparation Examples

Example 1

A mixture of 35.2 g (0.2 mole) of 2-hydrazino-4(3H)-quinazolinone, 250 ml of water, 30 ml of methanol and 36.6 ml of concentrated hydrochloric acid is stirred with 36.08 g (0.22 mole) of 1,1,3,3-tetramethoxy-propane at 40° C. The desired product precipitates after a short time from the solution initially formed. After a reaction of one hour in total at 40° C., 29.8 g of 2-(1H-pyrazol-1-yl)-4(3H)-quinazolinone (melting point 148°–50°) are isolated.

Examples 2 to 9

The following compounds are prepared analogously from the corresponding 2-hydrazino-4(3H)-quinazolinones and 1,1,3,3-tetramethoxy-propane:

Example 2

2-(1H-Pyrazol-1-yl)-6-bromo-4(3H)-quinazolinone; melting point: 210°–212°

Example 3

2-(1H-Pyrazol-1-yl)-5-chloro-4(3H)-quinazolinone; melting point: 195°–197°

Example 4

2-(1H-Pyrazol-1-yl)-6-chloro-4(3H)-quinazolinone; melting point: 217°–219°

Example 5

2-(1H-Pyrazol-1-yl)-7-chloro-4(3H)-quinazolinone; melting point: 221°–222°

Example 6

2-(1H-Pyrazol-1-yl)-6-fluoro-4(3H)-quinazolinone; melting point: 196°–197°

Example 7

2-(1H-Pyrazol-1-yl)-8-methyl-4(3H)-quinazolinone; melting point: 166°–167°

Example 8

2-(1H-Pyrazol-1-yl)-6-trifluoromethyl-4(3H)-quinazolinone; melting point: 220°–222°

Example 9

2-(1H-Pyrazol-1-yl)-6,7-dimethoxy-4(3H)-quinazolinone; melting point: 215°–217°

Example 10

149.2 g (1.32 moles) of 2-methyl-3-dimethylaminoacrolein are added all at once to a mixture, stirred at 40° C., of 211.2 g (1.2 moles) of 2-hydrazino-4(3H)-quinazolinone, 1.5 litres of water, 540 ml of methanol and 220 ml of concentrated hydrochloric acid. The suspension is stirred at 40° for a total of 4.5 hours and at 60° for 1.5 hours. The crude 2-(4-methyl-1H-pyrazol-1-yl)-4(3H)-quinazolinone isolated at room temperature is obtained in an amount of 245 g of melting point 169°–71°.

Examples 11 to 20

The following compounds are obtained similarly from the corresponding 2-hydrazino-4(3)-quinazolinones and 2-methyl-3-dimethylaminoacrolein or 2-ethyl-3-dimethylamino-acrolein:

Example 11

2-(4-Ethyl-1H-pyrazol-1-yl)-4(3H)-quinazolinone; melting point: 126°–127°

Example 12

2-(4-Methyl-1H-pyrazol-1-yl)-6-bromo-4(3H)-quinazolinone; melting point: 235°–236°

Example 13

2-(4-Ethyl-1H-pyrazol-1-yl)-5-chloro-4(3H)-quinazolinone; melting point: 132°–133°

Example 14

2-(4-Methyl-1H-pyrazol-1-yl)-6-chloro-4(3H)-quinazolinone; melting point: 209°–210°

Example 15

2-(4-Ethyl-1H-pyrazol-1-yl)-6-chloro-4(3H)-quinazolinone; melting point: 178°–179°

Example 16

2-(4-Methyl-1H-pyrazol-1-yl)-6-fluoro-4(3H)-quinazolinone; melting point: 187°–188°

Example 17

2-(4-Ethyl-1H-pyrazol-1-yl)-6-fluoro-4(3H)-quinazolinone; melting point: 149°–151°

Example 18

2-(4-Methyl-1H-pyrazol-1-yl)-8-methyl-4(3H)-quinazolinone; melting point: 169°–170°

Example 19

2-(4-Methyl-1H-pyrazol-1-yl)-6-trifluoromethyl-4(3H)-quinazolinone; melting point: 219°–220°

Example 20

2-(4-Ethyl-1H-pyrazol-1-yl)-6-trifluoromethyl-4(3H)-quinazolinone; melting point: 194°–195°

Example 21

57 ml (0.36 mole) of 2-isopropoxy-3-dimethylaminoacrolein are added all at once to a mixture, stirred at 40°, of 52.8 g (0.3 mole) of 2-hydrazino-4(3H)-quinazolinone, 375 ml of water, 45 ml of methanol and 55 ml of concentrated hydrochloric acid.

After the mixture has been warmed to 40° for 2 hours, 300 ml of water are added and the mixture is heated at 90° to 95° for 30 minutes. If necessary, the crude 2-(4-isopropoxy-1H-pyrazol-1-yl)-4(3H)-quinazolinone (53.2 g of melting point 165°–7°) can be recrystallized from n-propanol. The melting point is then 166° to 168° C.

Example 22

Isomer mixture of 2-(3-methyl-1H-pyrazol-1-yl)-4(3H)quinazolinone and 2-(5-methyl-1H-pyrazol-1-yl)-4(3H)quinazolinone 188.8 g (1.43 moles) of 4,4-dimethoxy-butan-2-one are added all at once to a suspension, stirred at 40°, of 228.8 g (1.3 moles) of 2-hydrazino-4(3H)-quinazolinone, 1625 ml of water, 195 ml of methanol and 238 ml of concentrated hydrochloric acid, and the mixture is kept at 40° for 1 hour. After the reaction, the reaction mixture is filtered with suction, and the residue is washed with water and dried; 267 g of crude product of melting point 138° to 141° C. are obtained. To remove sparingly soluble impurities, the product is stirred with 10 times the amount of toluene at 90°, the mixture is filtered and the filtrate is concentrated in vacuo. 240 g of the isomer mixture of melting point 139°–43° remain. According to the nuclear magnetic resonance spectrum, it contains 17% of the 3-methyl isomer and 83% of the 5-methyl isomer.

Example 23

2-(5-Methyl-1H-pyrazol-1-yl)-4(3H)-quinazolinone

The isomer mixture obtained according to Example 22 is recrystallized to constant melting point from 10 times the amount of ethanol. The pure 5-methyl compound of melting point 153° to 154° C. is obtained.

Example 24

35.2 g (0.2 mole) of 2-hydrazino-4(3H)-quinazolinone, 500 ml of ethanol and 31.68 g (0.24 mole) of 4,4-dimethoxy-butan-2-one are boiled under reflux for 4.5 hours. The initial suspension has then dissolved. The same volume of 2 N HCl at 50° is added at 50°, whereupon a precipitate soon forms. After warming at 50° for a total of 40 minutes, the 2-(3-methyl-1H-pyrazol-1-yl)-4(3H)-quinazolinone is isolated by filtration with suction. The crude product (35.9 g of melting point 162° to 165° C.) is recrystallized from ethanol and then has a melting point of 165° to 166° C.

Examples 25 to 28

The following compounds are obtained from the corresponding 2-hydrazino-4(3H)-quinazolinones by reaction with 4,4-dimethoxy-butan-2-one under analogous experimental conditions:

Example 25

2-(3-Methyl-1H-pyrazol-1-yl)-6-bromo-4(3H)-quinazolinone; melting point: 227°–228°

Example 26

2-(3-Methyl-1H-pyrazol-1-yl)-6-chloro-4(3H)-quinazolinone; melting point: 219°–221°

Example 27

2-(3-Methyl-1H-pyrazol-1-yl)-6-fluoro-4(3H)-quinazolinone; melting point: 186°–187°

Example 28

2-(3-Methyl-1H-pyrazol-1-yl)-6-trifluoromethyl-4(3H)-quinazolinone; melting point: 207°–208°

Example 29

96 g (0.5 mole) of 2-methylthio-4(3H)-quinazolinone are stirred in 250 ml of dimethylformamide with 142 g (1 mole) of 4-(β-methoxy-ethoxy)pyrazole at the reflux temperature for 40 hours. After cooling, 2.5 litres of water are added and a pH value of 3 is established with hydrochloric acid. The crude product which separates out (97.3 g of melting point 119°–24°) is recrystallized from isopropanol. 83.8 g of 2-(4-β-methoxyethoxy-1H-pyrazol-1-yl)-4(3H)-quinazolinone of melting point 125° to 127° C. are obtained.

Examples 30 and 31

If 4-chloro-pyrazole or 4-methoxy-pyrazole is used instead of the 4-(β-methoxy-ethoxy)-pyrazole, the following compounds are obtained in an analogous procedure:

Example 30

2-(4-Chloro-1H-pyrazol-1-yl)-4(3H)-quinazolinone; melting point: 234°–235°

Example 31

2-(4-Methoxy-1H-pyrazol-1-yl)-4(3H)-quinazolinone; melting point: 169°–170°

Example 32

12.3 g (0.05 mole) of 2-(1H-pyrazol-1-yl)-6-chloro-4(3H)-quinazolinone (=compound from Example 4) are stirred in 1 liter of water with 45 ml of 1 N KOH for 1 hour. Residues of the starting material which have remained undissolved are removed, the clear solution is evaporated in vacuo and the solid residue is dried at 110° C. to give 12.2 g of water-soluble potassium salt of the quinazolinone employed.

Use Examples

In the examples, the following active compounds are designated by the letters A to H:

A 2-(1H-Pyrazol-1-yl)-4-(3H)-quinazolinone
B 2-(4-Methyl-1H-pyrazol-1-yl)-4(3H)-quinazolinone
C 2-(3-Methyl-1H-pyrazol-1-yl)-4(3H)-quinazolinone
D 2-(5-Methyl-1H-pyrazol-1-yl)-4(3H)-quinazolinone
E Isomer mixture of 2-(3- and 5-methyl-1H-pyrazol-1-yl)-4(3H)-quinazolinone
F 2-(4-Ethyl-1H-pyrazol-1-yl)-4(3H)-quinazolinone
G 2-(4-Methyl-1H-pyrazol-1-yl)-6-chloro-4-(3H)-quinazolinone
H 2-(1H-Pyrazol-1-yl)-7-chloro-4(3H)-quinazolinone

Example 33

To demonstrate the activity against fungi, the minimum inhibitory concentrations (MIC) of active compounds according to the invention are determined:

Active compounds according to the invention are added in concentrations of 0.1 mg/l to 5,000 mg/l to an agar prepared from beerwort and peptone. After the agar has solidified, it is contaminated with pure cultures of the test organisms listed in the table. After storage at 28° C. and 60 to 70% relative atmospheric humidity for 2 weeks, the MIC is determined. The MIC is the lowest concentration of active compound at which no growth at all by the species of microbes used takes place, and is given in Table 1.

TABLE 1

MIC value data in mg/l for the action of substances according to the invention on fungi

| Active compound | Aspergillus niger | Alternaria tenuis | Aureobasidium pullulans | Chaetomium globosum | Coniophora puteana | Lentinus tigrinus | Penicillium glaucum | Polyporus versicolor | Sclerophoma pityophila | Trichoderma viride |
|---|---|---|---|---|---|---|---|---|---|---|
| A | 100 | 20 | 5 | 100 | 1 | 20 | 100 | 20 | 20 | 100 |
| B | 50 | 75 | 10 | <20 |  | <10 | 7 | <10 | 50 | 50 |
| C | 35 | 15 | 50 | 5 | <0.1 | 20 | 75 | 35 | 10 | 50 |
| D | 35 | 15 | 35 | 5 | <0.1 | 20 | 35 | 15 | 50 | 50 |
| E | 50 | 75 | 15 | 3 | 1 | 20 | 35 | 35 | 2 | 75 |
| F | 50 |  | 50 | <20 |  | 20 | 35 | 30 | 50 | 50 |
| G |  |  |  | 1 | 1 |  | 7 |  | 5 |  |

Example 34

(action against slime organisms)

Compounds according to the invention are used in concentrations of in each case 0.1 to 100 mg/l in Allens nutrient solution (Arch. Mikrobiol. 17, 34 to 53 (1952)), which contains, in 4 l of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam, dissolved in a little acetone. Shortly beforehand, the nutrient solutions are infected with slime organisms (about $10^6$ germs/ml), which have been isolated from the spinning water circulations used in the production of polyamide. Nutrient solutions which contain the minimum inhibitory concentration (MIC) or higher concentrations of active compound are still completely clear after culture for 3 weeks at room temperature, that is to say the pronounced reproduction of the microbes and slime formation noticeable after 3 to 4 days in nutrient solutions containing no active compounds are absent.

The following MIC values can be determined in this manner for the substances according to the invention:

| Active compound | MIC in mg/l |
|---|---|
| A | 30 |
| C | 100 |
| D | 75 |
| F | 30 |
| H | 100 |

Example 35

Testing of active compound E as a paint fungicide

Testing is carried out in accordance with the method in Report 219 of the Defense Standards Laboratories Maribyrnong/Australia as follows: a smooth card is coated on both sides with the paint to be tested and is dried at room temperature for 8 days. For ageing, part of the paint film is kept in running water of 24° for 24 hours, or aerated with fresh air of 40° to 60° C. for 8 days, or subjected to a dry Xenon test for 110 hours. Pieces of 5×5 cm cut out from the samples thus prepared are placed individually on a glucose nutrient medium in Petri dishes and contaminated with a spore suspension of the following fungi: *Aspergillus niger, Aureobasidium pullulans, Alternaria tenuis, Penicillium citrinum, Stachybotrys atra, Paecilomyces varioti, Cladosporium herbarum, Aspergillus ustus* and *Aspergillus flavus.*

The contaminated dishes are stored at 28° to 30° C. and 90 to 95% relative atmospheric humidity, and are evaluated after 3 weeks. Paint films are regarded as mould-resistant if the samples remain free from fungi after these tests.

A commercially available emulsion paint based on PVA is tested for mould resistance by the test method described above.

The following evaluation results from the test:

Paint films of the PVA emulsion paint containing 0.5% of the substance according to the invention are mould-resistant, even if they are exposed to the above-mentioned ageing processes before the microbiological testing.

In contrast, paint films of the PVA emulsion paint which contains tetramethylthiuram disulphide as the fungicide are only mould-resistant if they contain 4% of this fungicide.

Example 36

(with comparison)

Testing of active compound E as a preservative for cooling lubricants

3% of a preservative composed of 90% of benzyl alcohol mono(poly)hemiformal and 10% of active compound E is added to a cooling lubricant based on mineral oil.

3–5% strength use dilutions of the cooling lubricant are contaminated massively each day for 3 months with microbes (bacteria, yeasts and moulds) isolated from microbially decayed cooling lubricant use dilutions.

At the end of the testing period, the use dilutions are still germ-free; they have thus been reliably preserved.

In contrast, corresponding use dilutions containing only benzyl alcohol mono(poly)hemiformal show attack by mould at the end of the testing period; the preservation is accordingly inadequate.

What is claimed is:

1. A process for protecting a plant or an industrial material against microbial attack which comprises applying to said plant or industrial material or their habitat a microbicidal effective amount of a 2-(1H-pyrazol-1-yl)-4-(3H)-quinazolinone of the formula

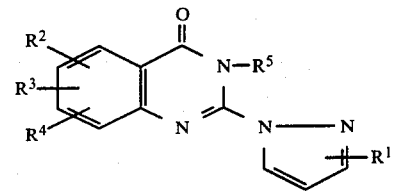

wherein

R¹, R², R³ and R⁴ are identical or different and denote hydrogen, halogen, $C_1$–$C_{12}$ alkyl, $C_1$–$C_{12}$ alkoxy, hydroxyl or amino and R represents hydrogen or a cation selected from alkali metal ions alkaline earth metal ions and ammonium ion.

2. A process according to claim 1 wherein said quinazolinone is applied to a plant or its habitat.

3. A process according to claim 1 wherein said quinazolinone is applied to an industrial material or its habitat.

4. A process according to claim 1 wherein said quinazolinone is applied to a plant in a fungicidally effective amount.

5. A process according to claim 1 wherein said quinazolinone is applied to an industrial material in a fungicidally effective amount.

6. A process according to claim 1 wherein said quinazolinone is applied to an industrial material in a bactericidally effective amount.

7. A process according to claim 1 wherein said quinazolinone is applied to an industrial material in a slimcidally effective amount.

8. A process according to claim 1 wherein said quinazolinone is applied to an industrial material in a moldicidally effective amount.

9. A process according to claim 1 wherein said quinazolinone is applied to said plant, industrial material or habitat in an amount of 0.001 to 5% by weight based upon the material to be protected.

10. A process according to claim 1 wherein said quinazolinone is 2-(1H-Pyrazol-1-yl)-4-(3H)-quinazolinone.

11. A process according to claim 1 wherein said quinazolinone is 2-(4-Methyl-1H-pyrazol-1-yl)-4(3H)-quinazolinone.

12. A process according to claim 1 wherein said quinazolinone is 2-(3-Methyl-1H-pyrazol-1-yl)-4(3H)-quinazolinone.

13. A process according to claim 1 wherein said quinazolinone is 2-(5-Methyl-1H-pyrazol-1-yl)-4(3H)-quinazolinone.

14. A process according to claim 1 wherein said quinazolinone is 2-(4-Ethyl-1H-pyrazol-1-yl)-4(3H)-quinazolinone.

15. A process according to claim 1 wherein said quinazolinone is 2-(4-Methyl-1H-pyrazol-1-yl)-6-chloro-4-(3H)-quinazolinone.

16. A process according to claim 1 wherein said quinazolinone is 2-(1H-Pyrazol-1-yl)-7-chloro-4(3H)-quinazolinone.

* * * * *